United States Patent [19]
Osawa et al.

[11] Patent Number: 5,516,764
[45] Date of Patent: May 14, 1996

[54] ANTI-INFLAMMATORY AGENT

[75] Inventors: Ryoichi Osawa, Iruma; Isao Suda, Tokorozawa; Masaaki Numata, Kawagoe; Mamoru Sugimoto; Kenkichi Tomita, both of Tokyo; Nobuyuki Kibushi, Iruma; Takayuki Ishii, Tokyo; Naokazu Sugiyama, Tokyo; Makiko Kasano; Tae Yasunaga, both of Tokorozawa; Makoto Tanaka, Higashimurayama; Tomoya Ogawa, Musashino; Mariko Ishii, Tokyo, all of Japan

[73] Assignee: Mect Corporation, Tokyo, Japan

[21] Appl. No.: 219,236

[22] Filed: Mar. 28, 1994

Related U.S. Application Data

[63] Continuation of Ser. No. 846,089, Mar. 5, 1992, abandoned.

[30] Foreign Application Priority Data

| Mar. 7, 1991 | [JP] | Japan | 3-067966 |
| Jul. 24, 1991 | [JP] | Japan | 3-208427 |
| Aug. 12, 1991 | [JP] | Japan | 3-226578 |

[51] Int. Cl.$^6$ .............. A61K 31/70; C07H 1/00; A01N 43/04
[52] U.S. Cl. ............... 514/54; 536/123.1; 536/123.12; 514/23; 514/53
[58] Field of Search .................. 530/395, 350, 530/402, 403; 536/1.11, 123.1; 514/23, 54, 53

[56] References Cited

U.S. PATENT DOCUMENTS

| 4,740,589 | 4/1988 | Moreno | 530/395 |
| 4,753,796 | 6/1988 | Moreno et al. | 536/127 |
| 5,116,752 | 5/1992 | Sugimori et al. | 435/252.1 |
| 5,310,881 | 5/1994 | Sakurai et al. | 530/395 |

FOREIGN PATENT DOCUMENTS

| 0145359 | 11/1984 | European Pat. Off. ............ 39/2 |
| 01299294 | 12/1989 | Japan . |
| 2-19393 | 1/1990 | Japan . |

OTHER PUBLICATIONS

Devi et al. *Proc. Natl. Acad. Sci.*, vol. 88, pp. 7175–7179, (Aug. 15, 1991).
Ebner et al. *Z. Gesamte Inn Med.*, vol. 29(21), pp. 899–903, (1974) [Abstract Only].
Komai et al. *Virology*, vol. 163(2), pp. 629–634, (1988). [Abstract Only].
Kai, H et al., "Anti–allergic Effect of N–Acetylneuraminic Acid in Guinea–pigs," *J. Pharm. Pharmacol.*, 1990, 42:773–777.
Nomoto et al., "Structures of Carbohydrate Units Isolated from Trout Egg Polysialoglycoproteins: Short–Cored Units with Oligosialosyl Groups," *Archives of Biochemistry and Biophysics*, 218:1, Oct. 1, 1982, pp. 335–341.
Davis et al., "Evidence for a Bladder Cell Glycolipid Receptor for *Escherichia coil* and the Effect of Neuraminic Acid and Colominic Acid on Adherence," *Infection and Immunity*, 34:3, Dec. 1981, pp. 944–948.
Piras et al., "The effect of fetuin and other sialoglycoproteins on the in vitro penetration of *Trypanosoma cruzi* trypomastigotes into fibroblastic cells," *Molecular and Biochemical Parasitology*, 22 1987), pp. 135–143.
Hirsch, R., The Journal of Immunology, vol. 127, No. 5 (1981) pp. 1740–1743.
Görög, P., Agents and Actions, vol. 8, No. 5 (1978) pp. 543–545.
Ito, H. et al, Japanese Pharmacology & Therapeutics, vol. 13, No. 7 (1985) pp. 479–494.
Y. Murata et al, The Japanese Journal of Pharmacology, Proceedings of 61st General.
Nomoto et al, Archives of Biochemmistry and Biophysics, vol. 218, (1982) pp. 335–341.
Kwiatkowski et al; J. Virol. 43(2):697–704 (1982).
Finne et al; J. Biol. Chem. 260(2):1265–1270 (1985).
Kwiatkowski et al; Methods in Enzymology 138:786–792 (1987).
Yamasaki et al; Biochem. 30:851–857 (Jan. 22, 1991).
Ferrero et al; Biochem. J. 280:575–579 (Dec. 15, 1991).

*Primary Examiner*—Douglas W. Robinson
*Assistant Examiner*—Howard C. Lee
*Attorney, Agent, or Firm*—Burns, Doane, Swecker and Mathis

[57] ABSTRACT

An anti-inflammatory drug comprising as the effective component at least one compound selected from the group consisting of colominic acid, partial hydrolysis products of colominic acid and pharmaceutically acceptable salts thereof. The drug is used as a drug for renal diseases, a drug for hepatitis, an immunomodulator and a drug for inhibiting the chemotaxis of neutrophil.

4 Claims, No Drawings

ANTI-INFLAMMATORY AGENT

This application is a continuation of application Ser. No. 07/846,089, filed Mar. 5, 1992, now abandoned.

BACKGROUND OF THE INVENTION

1. Field of the Invention

The present invention relates to an anti-inflammatory agent in which colominic acid, a partial hydrolysis product of colominic acid or a pharmaceutically acceptable salt thereof is contained as the effective component. In particular, the present invention relates to a therapeutic drug for renal diseases, a therapeutic drug for hepatitis, an immunomodulator and a drug for inhibition of chemotaxis of neutrophil, in which colominic acid, a partial hydrolysis product of colominic acid or a pharmaceutically acceptable salt thereof is contained as the effective component.

2. Description of the Related Art

Colominic acid is a homopolymer with a molecular weight of about 10,000 and is constituted with sialic acid (N-acetylneuraminic acid represented by NeuAc), and is a polysaccharide which is used as the standard for classification of the seratype of *E. coli, Meningitis diplococcus* and the like.

Colominic acid is prepared by culturing a microorganism such as a microorganism of *Escherichia* (see Japanese Patent Publication (JP-B-) (KOKOKU) No. 47-26319, Japanese Patent Disclosure (JP-A-) (KOKAI) No. 1-144989). Oligomers with the molecular weight smaller than that of colominic acid are obtained by partial hydrolysis of colominic acid (see H. Nomoto et al, Arch. Biochem. Biophys., vol. 218, pages 335–341(1982)).

However, the physiological activity of colominic acid and partial hydrolysis products thereof has not been studied in detail. It has been reported that N-acetylneuraminic acid which is a component unit of colominic acid exhibits an anti-virus action, an anti-inflammatory action and an anti-allergy action (See (a) Hirsch, R. L., The Journal of Immunology, Vol. 127, No. 5 (1981) pages 1740–1743, (b) Gorog, P., Agents and Actions, Vol. 8, No. 5 (1978) pages 543–545, (c) Hiromi Ito et al, Japanese Pharmacology & Therapeutics, Vol. 13, No. 7 (1985) pages 479–494, (d) Kai, H. et al, Journal of Pharmacy and Pharmacology, Vol. 42 (1990) pages 773–777.)

SUMMARY OF THE INVENTION

An object of the invention is to provide a novel pharmaceutical preparation using colominic acid and partial hydrolysis products of colominic acid.

The present invention relates to an anti-inflammatory drug comprising as the effective component at least one compound selected from the group consisting of colominic acid, partial hydrolysis products of colominic acid represented by the general formula (I) or pharmaceutically acceptable salts thereof.

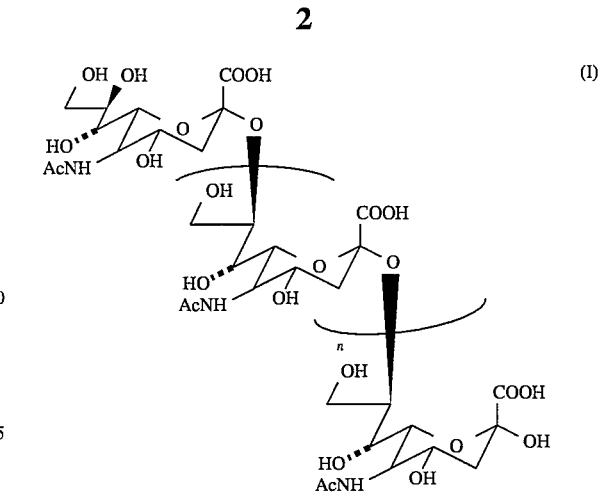

wherein n is an integer of from 0 to 10.

The invention is based on the discovery that colominic acid and partial hydrolysis products of colominic acid exhibit a suppressive action on renal inflammation, a suppressive action on platelet aggregation, a suppressive action on hepatitis, an immunomodulating action, and a suppressive action on the chemotactic activity of neutrophils which is stronger than that of a corticosteroid.

The present invention will be set forth below:

Partial hydrolysis products of colominic acid represented by the formula (I) are obtained by the method reported by Nomoto et al (Arch. Biochem. Biophys., vol. 218, pages 335–341 (1982)) from colominic acid which is commercially available. That is, colominic acid is partially hydrolyzed with hydrochloric acid and the hydrolysis product is subjected to fractionation using DEAE-Sephadex A-25 chromatography and the like to yield oligomers with 2 to 12 N-acetylneuraminic acid units which is represented by formula (I) (n=0–10). The number of the oligomer units n preferably ranges from 1 to 7.

Pharmaceutically acceptable salts of the compounds represented by formula (I) are also included in the present invention. Counter cations for formation of the salts are not limited, and examples of the cations include sodium, potassium, ammonium and amines.

The anti-inflammatory drug of the present invention can be administered orally or non-orally. Examples of the administration methods include eye drops, inhalations, internal uses, intramuscular injections, intracutaneous injections and intravenous injections. The administration amount is determined taking into account the type of disease, the degree of the disease and the weight of the patient and generally ranges from 0.1 to 1000 mg.

Fillers, binders, disintegrators, lubricants, film formers and the like may be used for the preparation of drugs orally administered.

Examples of the fillers include glucose, starch, milk sugar, mannitol, sorbitol, sugar, kaolin, dextrin, cyclodextrin, titanium oxide, calcium phosphate anhydride, soft silicic acid anhydride, talc, hydated natural magnesium silicate, precipitated calcium carbonate, magnesium metasilicate aluminate, crystalline cellulose and calcium carboxymethyl cellulose.

Examples of the binders include starch, dextrin, tragacanth gum, gelatin, polyvinyl pyrrolidone, polyvinyl alcohol, methyl cellulose, ethyl cellulose, hydroxyethyl cellusose, hydroxypropyl cellulose, hydroxypropyl methyl cellulose, hydroxypropyl starch, crystalline cellulose, pectin, polypectinic acid, sodium polypectinate, polyacrylic acid, sodium polyacrylate, polyacrylic acid copolymer, polymethacrylate, sodium polymethacrylate, polyhydroxymethyl acrylate, carboxymethyl cellulose, acacia and sodium alginate.

Examples of the disintegrators include starch, crystalline cellulose, carboxymethyl cellulose, calcium carboxymethyl cellulose, carboxymethyl starch, hydroxypropyl starch, agar powder and mannan.

Examples of the lubricants include talc, stearic acid, magnesium stearate, calcium stearate, hardened oil, sesame oil and parafins.

Examples of the film formers include cellulose derivatives such as ethyl cellulose (EC), carboxymethyl cellulose (CMEC), cellulose acetate (CA), cellulose acetate phthalate (CAP), hydroxypropyl methyl cellulose phthalate (HPMCP), methyl cellulose (MC), hydroxypropyl cellulose (HPC); polyvinyl derivatives such as polyvinyl acetal diethylamino acetate, methacrylic acid-ethylacrylate copolymer, methacrylic acid-methylmethacrylate copolyer, ethylmethacrylate-trimethylammonium ethyl chloride methacrylate copolymer and dimethylaminoethyl methacrylate-methyl methacrylate copolymer.

It would be possible to improve the properties of the film-formers by addition of various coating additives such as plasticizers for prevention of adhesion between particles of agents during the coating operations of the film-formers. Further the addition of the coating additives makes the coating operations easy.

Moreover, when the pharmaceutical drugs of the invention are used in the form of inhalants or injections, the following additives are used.

Calcium chloride, potassium chloride, sodium chloride, succinic acid, acetic acid, potassium acetate, sodium acetate, tartaric acid, potassium hydroxide, sodium hydroxide, parenteral solution, saline, sodium carbonate, sodium hydrocarbonate, lactic acid, sodium lactate, maleic acid, sulfuric acid, phophoric acid, potassium phosphate, sodium phosphate, potassium hydrogenphosphate, calcium hydrogenphosphate, potassium dihydrogenphosphate, sodium hydrogenphosphate, sodium dihydrogenphosphate, potassium pyrosulfite, sodium pyrosulfite, 1-arginine, purified egg yolk lecithin, purified gelatin, gelatin, milk sugar, human serum albumin, polyethylene glycol 400, polyethyl glycol 1500, polyethylene glycol 4000, polyethylene glycol 6000, polyoxyethylene hardening castor oil 60 and disodium edetate.

EXAMPLES

The invention will be illustrated in detail below:

It is provided that N-2, N-3, N-4, N-5, N-6, N-7, N-8, N-9 and N-12 represents sodium salts of partial hydrolysis products of colominic acid represented by formula (I) in which are n 0, 1, 2, 3, 4, 5, 6, 7 and 10 respectively.

Further N-30 represents sodium salt of colominic acid.

Example 1

Action to passive Arthus reaction.
(1) Experimental Animal
Hartly male guinea pigs with about 250 g of the body weight were used.
(2) Experimental materials Anti-ovalbumin rabbit serum (antibody titer=1/8000 or more) was used as the antiserum and ovalbumin was used as the antigen. The tested drug was commercially available sodium salt of colominic acid (available from Nakarai Kagaku in Japan) or was prepared in accordance with the method of Nomoto et al (Nomoto, H. et al, Arch. Boichem. Biophys. 218, pages 335–341 (1982)) by partial hydrolysis of colominic acid with an acid.

(3) Experimental method

Passive Arthus reaction was conducted in accordance with the method reported by Katayama et al (Katayama et al., Arzeim-Forsch., 31, page 1196 (1981)). That is, 2.5 ml/kg of anti-ovalbumin rabbit serum was injected intravenously into guinea pigs with about 250 g of the body weight to be sensitized. After 30 minutes, 0.050 ml of a solution containing the antigen was administered intracutaneously to the abdominal region, from which fur had been removed in advance, to allow the reaction to occur. Two hours after the challenge with the antigen, the bleeding area on the stimulated region was measured to indicate the degree of the reaction.

Alternatively, 30 minutes before the administration of the antigen, that is, just before the sensitization, the tested drug or saline was injected intravenously into guinea pigs of I to XI groups as shown below. Each group consisted of five guinea pigs.

| Group | Tested drug | Administration amount (per 1 kg of body weight) |
|---|---|---|
| I | colominic acid | 10 mg |
| II | N-2 | 10 mg |
| III | N-3 | 10 mg |
| IV | N-4 | 10 mg |
| V | N-5 | 10 mg |
| VI | N-6 | 10 mg |
| VII | N-7 | 10 mg |
| VIII | N-8 | 10 mg |
| IX | N-9 | 10 mg |
| X | N-12 | 10 mg |
| XI | Saline | 2.5 ml |

(4) Statistical treatment

Each group used 5 guinea pigs and the experimental results are shown by average ± standard deviation. Student's t test was used for the test for significance and $P<0.05$ was evaluated statistically significant.

(5) Experimental results

Table 1 shows bleeding areas on the stimulated regions of groups I to XI. Each value was the suppression ratio calculated on the basis of the data obtained from group XI (administered with saline). In Groups I to X, the bleeding areas on the stimulated regions were significantly suppressed.

TABLE 1

| | TESTED DRUGS | SUPPRESSION RATE |
|---|---|---|
| I | (Colominic acid 10 mg/Kg) | 66.4 ± 4.3**% |
| II | (N-2 10 mg/Kg) | 67.2 ± 2.5**% |
| III | (N-3 10 mg/Kg) | 70.7 ± 3.8**% |
| IV | (N-4 10 mg/Kg) | 72.3 ± 2.4**% |
| V | (N-5 10 mg/Kg) | 82.9 ± 3.2**% |
| VI | (N-6 10 mg/Kg) | 87.8 ± 2.5**% |
| VII | (N-7 10 mg/Kg) | 80.9 ± 2.9**% |
| VIII | (N-8 10 mg/Kg) | 79.9 ± 2.7**% |
| IX | (N-9 10 mg/Kg) | 70.6 ± 3.1**% |
| X | (N-12 10 mg/Kg) | 71.3 ± 3.3**% |

**Significant difference from control ($p < 0.01$)

(6) Judgement

The results of the passive Arthus reactions show that colominic acid and the partial hydrolysis products of colominic acid exhibit the suppression effect on the allergy type III reaction.

Example 2

In accordance with the procedures of Example 1, except that 10 mg, 30 mg or 100 mg (per 1 kg body weight of guinea pig) of N-7 was orally administered 1 hour before the administration of the antigen, the passive Arthus reaction was conducted. The results are shown in Table 2.

TABLE 2

| TESTED DRUGS | SUPPRES-SION RATE(%) 0.05 mg | SUPPRES-SION RATE(%) 0.025 mg |
| --- | --- | --- |
| N-7 10 mg/Kg p.o. (po) 30 min before | 70.8 ± 25.7** | 75.5± 34.2** |
| N-7 10 mg/Kg s.c. (sc) 1 hr before | 61.0 ± 4.3** | 63.6± 12.3** |
| N-7 30 mg/Kg s.c. (sc) 1 hr before | 57.8 ± 8.7** | 64.3± 7.9** |
| N-7 100 mg/Kg s.c. (sc) 1 hr before | 45.9 ± 3.5** | 54.8± 9.9** |

**Significantly difference from control ($p < 0.01$)
***Significantly difference from control ($p < 0.001$)

The results of passive Arthus reaction shown in Table 2 show that colominic acid and the partial hydrolysis products of colominic acid exhibit the suppression effect on the allergy type III reaction.

Example 3

Action on puromycin aminonucleocide (PAN) nephritis (1) Experimental Animals

Sprague-Dawley (SD) male rats with 160–180 g of the body weight were used.

(2) Experimental Materials

PAN was perchased from Sigma in USA. The tested drugs were obtained in the same manner as those of Example 1.

(3) Experimental Method

Eighty mg (per 1 kg of the body weight) of PAN was administered intraperitoneally to induce nephritis. Then the following tested drugs (Group I, II, III, IV, V, VI, VII, VIII) or saline (Group IX, X) were administered continuously and subcutaneously or orally once a day to the above rats just after the administration of PAN for 15 days. Rats of group XI were administered continuously and intracutaneously with methylprednisolone as the control drug once a day from just after the administration of PAN for 15 days.

After 3, 6, 9 and 13 days, 5 ml of water was supplied and urine was collected for 6 hours respectively. Fourteen days after the administration of PAN, rats were dissected and the kidneys were picked out, and the wet weight of the kidneys were measured.

| Group | Tested drug | Administration amount (per 1 kg of body weight) |
| --- | --- | --- |
| I | N-6 | 10 mg (oral) |
| II | N-6 | 5 mg (oral) |
| III | N-6 | 5 mg (intracutaneous) |
| IV | N-6 | 1 mg (intracutaneous) |
| V | colominic acid | 30 mg (oral) |
| VI | colominic acid | 10 mg (oral) |
| VII | colominic acid | 20 mg (intracutaneous) |
| VIII | colominic acid | 5 mg (intracutaneous) |
| IX | Saline | 2.5 ml (oral) |
| X | Saline | 2.5 ml (intracutaneous) |
| XI | methylprednisolone | 2 mg (intracutaneous) |

(4) Statistical treatment

Each group used 10 rats and the experimental results are shown by average± standard deviation. Student's t test was used for the test for significance and $p<0.05$ was evaluated statistically significant.

(5) Experimental results

① Increasing ratio of the body weight and the wet weight of the kidneys of group I–XII are shown in Table 3. The increases of the body weight were suppressed by the administration of PAN (IX and X) but the suppression of the increases of the body weight was prevented and the improvements in the general symptoms were observed in the groups administered with N-6 (groups I–IV) and colominic acid (groups V–VIII). On the other hand, in the group administered with methylprednisolone as the control drug (group XI), the improvements in the increases of the body weight and the general symptoms were not observed.

Although the wet weight of the kidneys was increased by the administration of PAN (groups XI and XX), the increases of the wet weight of the kidneys were suppressed in the groups administered with N-6 (groups I–IV) and colominic acid (groups V–VIII). The same degree of the suppression efftct was observed in the group administered with methylprednisolone, the positive control drug (group XI).

TABLE 3

| | TESTED DRUGS | INCREASE RATE OF WEIGHT (%) | KIDNEY WEIGHT RATE g/100 g BW |
| --- | --- | --- | --- |
| I | N-6 10 mg/Kg p.o.(po) | 152.6 ± 1.5 | 0.83 ± 0.04 |
| II | N-6 5 mg/Kg p.o.(po) | 149.3 ± 1.9 | 0.87 ± 0.06 |
| III | N-6 5 mg/Kg s.c.(sc) | 155.2 ± 1.7 | 0.77 ± 0.03 |
| IV | N-6 1 mg/Kg s.c.(sc) | 152.1 ± 1.3 | 0.84 ± 0.04 |
| V | Colominic acid 30 mg/Kg p.o.(po) | 145.8 ± 1.5 | 0.89 ± 0.04 |
| VI | Colominic acid 10 mg/Kg p.o.(po) | 144.6 ± 2.4 | 0.98 ± 0.07 |
| VII | Colominic acid 20 mg/Kg s.c.(sc) | 150.2 ± 2.3 | 0.81 ± 0.04 |
| VIII | Colominic acid 5 mg/Kg s.c.(sc) | 150.0 ± 1.9 | 0.92 ± 0.06 |
| IX | saline 2.5 ml/Kg p.o.(po) | 130.5 ± 1.9 | 0.94 ± 0.05 |
| X | saline 2.5 ml/Kg s.c.(sc) | 129.8 ± 2.0 | 1.00 ± 0.04 |
| XI | Methyprednisolone 2 mg/Kg s.c.(sc) | 125.1 ± 1.4 | 0.83 ± 0.05 |
| XII | Normal Animal without PAN | 164.8 ± 1.9 | 0.73 ± 0.02 |

② The amount of protein contained in the urine collected from groups I–XII on the days 3, 6, 9 and 13 is shown in Table 4. The amount of protein contained in the urine was increased from day 6 by the administration of PAN (groups IX, X). The increases of the amount of protein in the urine was suppressed in the groups administered with N-6 (groups I–IV) and with colominic acid (groups V–VIII) on days 6, 9 and 13 in a dose-dependent manner. The same degree of the suppressive effect was observed in the group administered with methylprednisolone, the positive control drug (group XI).

TABLE 4

| | TESTED DRUGS | PROTEINS IN URINE (mg/24 hrs) | | | |
|---|---|---|---|---|---|
| | | DAY 3 | DAY 6 | DAY 9 | DAY 13 |
| I | N-6 10 mg/Kg p.o.(pc) | 7.3 ± 0.9 | 35.8 ± 6.7 | 70.6 ± 10.9 | 70.3 ± 12.7 |
| II | N-6 5 mg/Kg p.o.(po) | 8.1 ± 1.0 | 39.4 ± 8.3 | 71.6 ± 14.5 | 79.0 ± 17.3 |
| III | N-6 5 mg/Kg s.c.(sc) | 7.7 ± 0.6 | 27.8 ± 5.6 | 35.9 ± 7.1 | 40.0 ± 9.7 |
| IV | N-6 1 mg/Kg s.c.(sc) | 7.9 ± 0.5 | 34.7 ± 8.5 | 58.4 ± 11.4 | 58.4 ± 11.7 |
| V | Colominic acid 30 mg/Kg p.o.(po) | 8.6 ± 0.9 | 33.8 ± 7.7 | 66.6 ± 16.7 | 74.8 ± 22.7 |
| VI | Colominic acid 10 mg/Kg p.o.(po) | 7.7 ± 0.7 | 32.6 ± 9.4 | 68.6 ± 14.6 | 87.0 ± 23.3 |
| VII | Colominic acid 20 mg/Kg s.c.(sc) | 7.5 ± 0.5 | 23.8 ± 5.9 | 43.9 ± 9.3 | 53.0 ± 11.7 |
| VIII | Colominic acid 5 mg/Kg s.c.(sc) | 7.9 ± 0.7 | 31.6 ± 9.2 | 66.4 ± 15.8 | 76.9 ± 19.7 |
| IX | saline 2.5 ml/Kg p.o.(Po) | 9.5 ± 2.1 | 109.5 ± 17.7 | 145.9 ± 29.1 | 236.4 ± 43.6 |
| X | saline 2.5 ml/Kg s.c.(sc) | 8.0 ± 0.9 | 122.3 ± 13.8 | 141.7 ± 12.5 | 194.9 ± 13.1 |
| XI | Methprednisolone 2 mg/Kg s.c.(sc) | 14.9 ± 1.6 | 35.4 ± 12.9 | 42.4 ± 12.8 | 39.2 ± 9.0 |
| XII | Normal Animal without PAN | 6.5 ± 0.7 | 11.3 ± 0.3 | 15.7 ± 2.5 | 16.3 ± 1.7 |

(6) Judgement

The results of the above PAN nephritis experiments show that the oral or intracutaneous administrations of colominic acid or N-6 have the suppressive effects on nephritis.

Example 4

Action on the arachidonic acid-induced death
(1) Experimental Animals
ddy male mice with 20–25 g of the body weight were used.
(2) Experimental Materials
Arachidonic acid was purchased from Sigma in USA. The tested drugs were obtained by the same manners as those described in Example 1.
(3) Experimental Method
The following tested drugs (groups I, II) or saline (group III) were administered intraperitoneally to the mice. The mice of group IV were administered intraperitoneally with aspirin as the control. Thirty minutes later after the administration of the tested drugs, 100 mg (per 1 kg of the body weight) of arachidonic acid was administered to the tail vein of the mice intravenously and the period (seconds) until death was measured. It is provided that in the case where a mouse was alive for 5 minutes or more, the period was shown as 300 seconds.

| Group | Tested drug | Administration amount (per 1 kg of body weight) |
|---|---|---|
| I | saline | 0.2 mg |
| II | N-6 | 10 mg |
| III | colominic acid | 10 mg |
| IV | aspirin | 30 mg |

(4) Statistical treatment
Each group used 10 mice and the experimental results are shown by average ± standard deviation. Student's t test was used for the test for significance and P<0.05 was evaluated statistically significant.
(5) Experimental results
The time period to death (sec) and the survival rates of groups I–IV are shown in Table 5. In groups II and III, the periods to death were prolonged significantly in comparison with group I (group administered with saline) and the survival rates were increased. In group IV administered with aspirin, the control drug, the same degree of the effect was observed.

TABLE 5

| | TESTED DRUGS | PERIOD TO DEATH (SEC) | SURVIVAL RATE (%) |
|---|---|---|---|
| I | saline 0.2 ml Intraperitoneal | 89.5 ± 9.6 | 0% (0/10) |
| II | N-6 10 mg/Kg Intraperitoneal | 216.0 ± 34.6* | 50% (5/10) |
| III | Colominic acid 10 mg/Kg Intraperitoneal | 193.5 ± 35.5*** | 60% (6/10) |
| IV | aspirin 10 mg/Kg Intraperitoneal | 234.5 ± 29.6** | 60% (6/10) |

*$p < 0.05$, $p < 0.01$, *$p < 0.001$ (6) Judgement
The results of the arachidonic acid experiments show that colominic acid and N-6 exhibit the suppressive effect on the platelet aggregation.

Example 5

Action or galactosamine-induced hepatitis
(1) Experimental Animals
Wister male rats with 200–250 g of the body weight were used.
(2) Experimental Materials
D-galactosamine hydrochloride was obtained from Sigma in USA. The partial hydrolysis products of colominic acid were prepared by hydrolysis of colominic acid with an acid and purification.
(3) Experimental Method
Two hundred mg (per 1 kg of the body weight) of galactosamine was administered intraperioneally to rats to induce hepatitis. The tested drugs (groups II–XIII) or saline (group I) were administered intracutaneously 30 minutes before the administration of galactosamine as listed below. Two-4 hours after to the administration, the blood was collected under light anesthesia with ether, and glutamic-oxaloacetic-transaminase (GOT), glutamic-pyruvic transaminase (GPT) and alkaline phosphatase (ALP) in the blood were measured.

| Group | Tested drug | Administration amount (per 1 kg of rat body weight) |
|---|---|---|
| I | saline | 5.0 ml |
| II | N-3 | 30 mg |
| III | N-3 | 100 mg |
| IV | N-3 | 300 mg |
| V | N-6 | 30 mg |
| VI | N-6 | 100 mg |

-continued

| Group | Tested drug | Administration amount (per 1 kg of rat body weight) |
|---|---|---|
| VII | N-6 | 300 mg |
| VIII | N-9 | 30 mg |
| IX | N-9 | 100 mg |
| X | N-9 | 300 mg |
| XI | colominic acid | 30 mg |
| XII | colominic acid | 100 mg |
| XIII | colominicacid | 300 mg |

(4) Results

To illustrate the suppression of the galactosamine-induced hepatitis, the ratios of each biochemical value of groups II–XIII against that of group I (saline-administered group (100 %)) were listed in Table 6. Colominic acid and the partial hydrolysis products of colominic acid suppressed the increases of GOT, PGP and ALP induced by the administration of galactosamine in a dose-dependent manner.

TABLE 6

| Group | | GOT (Karmen) | GPT (Karmen) | ALP (IU) |
|---|---|---|---|---|
| II | (N-3: 30 mg/kg) | 2.34 | 1.65 | 2.89 |
| III | (N-3: 30 mg/kg) | 8.96 | 9.18 | 1.65 |
| IV | (N-3: 100 mg/kg) | 13.22* | 12.94* | 4.99 |
| V | (N-6: 300 mg/kg) | 5.53 | 2.45 | 10.22* |
| VI | (N-6: 30 mg/kg) | 26.96* | 2.86 | 12.65*** |
| VII | (N-6: 100 mg/kg) | 36.94 | 35.54* | 12.13** |
| VIII | (N-9: 300 mg/kg) | 4.55 | 3.59 | 8.65* |
| IX | (N-9: 30 mg/kg) | 20.56* | 16.530 | 9.10* |
| X | (N-9: 100 mg/kg) | 22.34* | 22.91* | 10.23* |
| XI | (Colominic acid: 30 mg/kg) | 2.86 | 2.67 | 2.36 |
| XII | (Colominic acid: 100 mg/kg) | 10.98 | 15.83 | 2.77 |
| XIII | (Colominic acid: 300 mg/kg) | 15.63* | 14.96* | 5.66 |

Significant differences from galactosamine-administered group *$0.01 < p \leq 0.05$, $0.001 \leq p < 0.01$, * $p \leq 0.001$ Example 6

( 1 ) Experimental Materials and Method
N-1 (sodium salt of sialic acid:sialic acid unit=1)
N-3 (partial hydrolysis product:sialic acid unit=3)
N-6 (partial hydrolysis product:sialic acid unit=6)
N-9 (partial hydrolysis product:sialic acid unit=9)
N-12 (partial hydrolysis product:sialic acid unit =12)
N-30 (colominic acid sodium salt:sialic acid unit=about 30)

(2) Experimental Animals

DBA/1 mice (male) 8 week-old were used.

It is provided that cyclosporin (CsA:Sandimmum internal use solution: Sankyo in Japan) was used as the positive control.

(3) Preparation of collagen arthritis model

Chicken collagen type II (hereinafter refer to IIC, Genzyme in USA) was dissolved in 0.02M Tris-0.15M sodium chloride buffer solution (pH 8.0) (4 mg/ml ) and mixed with the same volume of Freund's complete adjuvant (FCA) to prepare an emulsion. The emulsion (0.05 ml (100 μg/mouse) was injected to the left hindpaws of the mice on day 0 as the initial immunization. Then as the booster injection, the same amount of the emulsion prepared by the use of Freund's incomplete adjuvant (FIA) in place of the above FCA was injected to the base of the tail of the mice on day 21.

(4) Administration method and schedule

N-1, N-3, N-6, N-9, N-12 and N-30 were dissolved in saline and 5 mg/kg was administered intraperitoneally (ip) and continuously for 2 weeks. CsA was dissolved in olive oil and 50 mg/kg was administered orally according to the same schedule as the above. As the control group, saline was administered intraperitoneally.

(5) Measured items and measuring method (a) Arthritis incidence

Mice having an inflammatory score of/or greater obtained in the following item (b) were defined as mice with arthritis, and the arthritis incidence was calculated from the number of the mice with arthritis.

(b) Arthritis score

The arthritis strength of both of the forepaws and the right hindpaw which were not affected by the primary inflammatory was represented by the six uclues of from 0 to 5 points and the inflammatory scores were estimated on the basis of the full score 15 points.

(c) Change of body weight (6) Statistical treatment incidence, were subjected to Student's t test for significance to the control group and the effects were judged.

(Results)

(1) Arthritis incidence

TABLE 7

| WEEK | DAY | CONTROL | CsA | N-1 | N-3 | N-6 | N-9 | N-12 | N-30 |
|---|---|---|---|---|---|---|---|---|---|
| 0 | 0 | 0.0 | 0.0 | 0.0 | 0.0 | 0.0 | 0.0 | 0.0 | 0.0 |
| 0 | 1 | 0.0 | 0.0 | 0.0 | 0.0 | 0.0 | 0.0 | 0.0 | 0.0 |
| 0 | 3 | 0.0 | 0.0 | 0.0 | 0.0 | 0.0 | 0.0 | 0.0 | 0.0 |
| 0 | 5 | 0.0 | 0.0 | 0.0 | 0.0 | 0.0 | 0.0 | 0.0 | 0.0 |
| 1 | 8 | 0.0 | 0.0 | 0.0 | 0.0 | 0.0 | 0.0 | 0.0 | 0.0 |
| 1 | 11 | 0.0 | 0.0 | 0.0 | 0.0 | 0.0 | 0.0 | 0.0 | 0.0 |
| 2 | 14 | 0.0 | 0.0 | 0.0 | 0.0 | 0.0 | 0.0 | 0.0 | 0.0 |
| 3 | 21 | 0.0 | 0.0 | 0.0 | 0.0 | 0.0 | 0.0 | 0.0 | 0.0 |
| 4 | 29 | 0.0 | 0.0 | 0.0 | 62.5 | 25.0 | 12.5 | 37.5 | 0.0 |
| 5 | 36 | 100.0 | 37.0 | 50.0 | 75.0 | 25.0 | 50.0 | 75.0 | 25.0 |
| 6 | 42 | 100.0 | 25.0 | 50.0 | 75.0 | 25.0 | 75.0 | 100.0 | 62.5 |
| 7 | 49 | 100.0 | 37.5 | 50.0 | 87.5 | 25.0 | 75.0 | 100.0 | 62.5 |
| 8 | 56 | 100.0 | 25.0 | 62.5 | 75.0 | 50.0 | 75.0 | 100.0 | 62.5 |
| 9 | 63 | 100.0 | 50.0 | 75.0 | 87.5 | 62.5 | 87.5 | 100.0 | 75.0 |
| 10 | 70 | 100.0 | 62.5 | 87.5 | 87.5 | 75.0 | 87.5 | 100.0 | 75.0 |
| 11 | 76 | 100.0 | 62.5 | 75.0 | 75.0 | 75.0 | 87.5 | 100.0 | 75.0 |
| 12 | 84 | 100.0 | 62.5 | 75.0 | 87.5 | 62.5 | 87.5 | 100.0 | 62.5 |
| 13 | 91 | 87.5 | 50.0 | 75.0 | 100.0 | 75.0 | 87.5 | 100.0 | 75.0 |
| 14 | 98 | 87.5 | 50.0 | 87.5 | 87.5 | 75.0 | 100.0 | 100.0 | 62.5 |
| 15 | 105 | 87.5 | 50.0 | 87.5 | 75.0 | 50.0 | 100.0 | 75.0 | 75.0 |

TABLE 7-continued

| WEEK | DAY | CONTROL | CsA | N-1 | N-3 | N-6 | N-9 | N-12 | N-30 |
|---|---|---|---|---|---|---|---|---|---|
| 17 | 120 | 62.5 | 37.5 | 75.0 | 87.5 | 50.0 | 50.0 | 87.5 | 25.0 |

(2) Arthritis score

In the control group, 100% of the mice showed the symptoms of arthritis 5 weeks after the initial immunization (2 weeks after the booster injection), that is, the erythema and swelling were observed on the joints of the forepaws and hindpaws. The symptoms were reduced gradually from the peak (arthritis score: about 7) at week 6 and the arthritis incidence was continued at 100% to week 12.

The arthritis incidence and the arthritis scores were suppressed by the administration of N-1, N-3, N-6, N-9, N-12 or N-30 excepting for N-12. This tendency was continued to week 9 and, in particular, was remarkable from the initial period, when the symptoms appeared, to week 5–7 when the symptoms showed the peak.

TABLE 8

ARTHRITIS SCORE

| WEEK | DAY | CONTROL | CsA 50 mg/kg | N-1 5 mg/kg | N-3 5 mg/kg |
|---|---|---|---|---|---|
| 0 | 0 | 0.00 ± 0.00 | 0.00 ± 0.00 | 0.00 ± 0.00 | 0.00 ± 0.00 |
| 0 | 1 | 0.00 ± 0.00 | 0.00 ± 0.00 | 0.00 ± 0.00 | 0.00 ± 0.00 |
| 0 | 3 | 0.00 ± 0.00 | 0.00 ± 0.00 | 0.00 ± 0.00 | 0.00 ± 0.00 |
| 0 | 5 | 0.00 ± 0.00 | 0.00 ± 0.00 | 0.00 ± 0.00 | 0.00 ± 0.00 |
| 1 | 8 | 0.00 ± 0.00 | 0.00 ± 0.00 | 0.00 ± 0.00 | 0.00 ± 0.00 |
| 1 | 11 | 0.00 ± 0.00 | 0.00 ± 0.00 | 0.00 ± 0.00 | 0.00 ± 0.00 |
| 2 | 14 | 0.00 ± 0.00 | 0.00 ± 0.00 | 0.00 ± 0.00 | 0.00 ± 0.00 |
| 3 | 21 | 0.00 ± 0.00 | 0.00 ± 0.00 | 0.00 ± 0.00 | 0.00 ± 0.00 |
| 4 | 29 | 0.00 ± 0.00 | 0.00 ± 0.00 | 0.00 ± 0.00 | 0.00 ± 0.00 |
| 5 | 36 | 4.13 ± 2.42 | 0.63 ± 1.06** | 1.75 ± 1.98* | 2.13 ± 2.70 |
| 6 | 42 | 6.63 ± 3.02 | 1.13 ± 2.10*** | 2.63 ± 3.07** | 2.13 ± 2.70** |
| 7 | 49 | 4.88 ± 2.10 | 1.25 ± 2.05** | 2.25 ± 2.66* | 2.13 ± 2.23* |
| 8 | 56 | 4.38 ± 2.00 | 1.13 ± 2.10** | 2.75 ± 2.71 | 2.63 ± 2.26 |
| 9 | 63 | 4.38 ± 2.07 | 1.25 ± 1.83** | 3.13 ± 2.53 | 3.75 ± 2.71 |
| 10 | 70 | 4.63 ± 2.20 | 2.25 ± 2.43 | 2.75 ± 1.98 | 3.00 ± 2.00 |
| 11 | 76 | 4.50 ± 1.85 | 2.00 ± 2.00* | 2.63 ± 2.13 | 3.25 ± 2.31 |
| 12 | 84 | 3.75 ± 1.91 | 1.63 ± 1.77* | 3.25 ± 3.20 | 3.50 ± 2.45 |
| 13 | 91 | 3.88 ± 2.10 | 1.25 ± 1.49* | 2.75 ± 2.66 | 3.13 ± 1.46 |
| 14 | 98 | 2.25 ± 1.49 | 1.25 ± 1.49 | 2.25 ± 1.75 | 3.00 ± 1.77 |
| 15 | 105 | 2.25 ± 1.67 | 1.00 ± 1.31 | 2.25 ± 1.91 | 2.63 ± 2.00 |
| 17 | 120 | 1.25 ± 1.39 | 0.75 ± 1.16 | 1.63 ± 1.85 | 2.13 ± 1.13 |

*$0.01 < P \leq 0.05$
**$0.001 < P \leq 0.01$
***$P \leq 0.001$

TABLE 9

ARTHRITIS SCORE

| WEEK | DAY | N-6 5 mg/kg | N-9 5 mg/kg | N-12 5 mg/kg | N-30 5mg/kg |
|---|---|---|---|---|---|
| 0 | 0 | 0.00 ± 0.00 | 0.00 ± 0.00 | 0.00 ± 0.00 | 0.00 ± 0.00 |
| 0 | 1 | 0.00 ± 0.00 | 0.00 ± 0.00 | 0.00 ± 0.00 | 0.00 ± 0.00 |
| 0 | 3 | 0.00 ± 0.00 | 0.00 ± 0.00 | 0.00 ± 0.00 | 0.00 ± 0.00 |
| 0 | 5 | 0.00 ± 0.00 | 0.00 ± 0.00 | 0.00 ± 0.00 | 0.00 ± 0.00 |
| 1 | 8 | 0.00 ± 0.00 | 0.00 ± 0.00 | 0.00 ± 0.00 | 0.00 ± 0.00 |
| 1 | 11 | 0.00 ± 0.00 | 0.00 ± 0.00 | 0.00 ± 0.00 | 0.00 ± 0.00 |
| 2 | 14 | 0.00 ± 0.00 | 0.00 ± 0.00 | 0.00 ± 0.00 | 0.00 ± 0.00 |
| 3 | 21 | 0.00 ± 0.00 | 0.00 ± 0.00 | 0.00 ± 0.00 | 0.00 ± 0.00 |
| 4 | 29 | 0.25 ± 0.46 | 0.13 ± 0.35 | 1.00 ± 1.77 | 0.00 ± 0.00 |
| 5 | 36 | 0.25 ± 0.46** | 2.50 ± 3.30 | 2.25 ± 2.05 | 0.25 ± 0.46** |

TABLE 9-continued

ARTHRITIS SCORE

| WEEK | DAY | N-6 5 mg/kg | N-9 5 mg/kg | N-12 5 mg/kg | N-30 5mg/kg |
|---|---|---|---|---|---|
| 6 | 42 | 0.25 ± 0.46*** | 2.88 ± 3.09* | 3.88 ± 1.73* | 2.63 ± 3.81* |
| 7 | 49 | 0.88 ± 2.10** | 2.63 ± 2.77 | 4.38 ± 3.11 | 2.88 ± 3.76 |
| 8 | 56 | 1.50 ± 2.73* | 3.75 ± 2.76 | 4.00 ± 2.67 | 3.63 ± 4.00 |
| 9 | 63 | 2.50 ± 2.56 | 3.50 ± 2.73 | 3.88 ± 2.47 | 3.75 ± 3.73 |
| 10 | 70 | 2.75 ± 2.92 | 5.00 ± 2.98 | 5.25 ± 2.87 | 3.13 ± 3.04 |
| 11 | 76 | 2.38 ± 2.67 | 4.13 ± 2.70 | 5.50 ± 2.39 | 2.63 ± 2.88 |
| 12 | 84 | 2.00 ± 2.78 | 3.63 ± 2.20 | 3.63 ± 2.39 | 2.13 ± 2.36 |
| 13 | 91 | 2.63 ± 2.83 | 3.50 ± 1.93 | 4.38 ± 1.69 | 2.13 ± 2.23 |
| 14 | 98 | 2.13 ± 2.10 | 2.63 ± 1.69 | 3.25 ± 1.49 | 1.75 ± 2.12 |
| 15 | 105 | 1.50 ± 2.14 | 2.63 ± 2.07 | 2.25 ± 1.83 | 1.63 ± 1.69 |
| 17 | 120 | 1.38 ± 1.60 | 1.00 ± 1.20 | 1.50 ± 0.93 | 0.63 ± 1.19 |

*$0.01 < P \leq 0.05$
**$0.001 < P \leq 0.01$
***$P \leq 0.001$ (3) Body weight

In the control group, the suppressive tendency of the body weight increases was observed just after the initial and the booster injection, and after the symptoms of arthritis appeared. In the groups administered with CsA and N-1, N-3, N-6, N-9, N-12 and N-30, the suppressive tendency of the body weight increase which was assumed to be happened by the arthritis was improved. It is provided that the reductions in body weight which were assumed to be an adverse reaction were observed during the administration period of CsA. However, such a kind of adverse reaction was not observed in the group administered with N-1, N-3, N-6, N-9, N-12 and N-30.

TABLE 10

BODY WEIGHT (g)

| WEEK | DAY | CONTROL | CsA 50 mg/kg | N-1 5 mg/kg | N-3 5 mg/kg |
|---|---|---|---|---|---|
| 0 | 0 | 20.5 ± 0.8 | 20.5 ± 1.0 | 20.4 ± 0.6 | 20.4 ± 1.0 |
| 0 | 1 | 21.0 ± 1.1 | 20.8 ± 0.8 | 21.1 ± 0.5 | 20.7 ± 1.1 |
| 0 | 3 | 20.5 ± 1.0 | 19.6 ± 0.7* | 21.0 ± 0.8 | 20.8 ± 1.2 |
| 0 | 5 | 20.3 ± 1.0 | 19.3 ± 0.9* | 20.6 ± 0.5 | 20.5 ± 1.3 |
| 1 | 8 | 20.2 ± 0.9 | 20.0 ± 0.8 | 20.8 ± 0.7 | 20.4 ± 1.3 |
| 1 | 11 | 21.1 ± 1.0 | 20.0 ± 1.0* | 21.8 ± 0.8 | 21.2 ± 0.9 |
| 2 | 14 | 21.7 ± 1.0 | 21.3 ± 1.2 | 22.8 ± 0.8* | 21.9 ± 0.9 |
| 3 | 21 | 21.9 ± 1.0 | 22.2 ± 1.2 | 22.6 ± 0.8 | 22.0 ± 0.8 |
| 4 | 29 | 22.5 ± 1.1 | 22.9 ± 1.2 | 23.7 ± 1.1* | 22.9 ± 0.9 |
| 5 | 36 | 22.2 ± 1.0 | 23.2 ± 1.6 | 23.3 ± 1.4 | 23.1 ± 0.9 |
| 6 | 42 | 22.3 ± 0.9 | 24.0 ± 1.5* | 23.9 ± 1.6* | 24.0 ± 0.9** |
| 7 | 49 | 22.8 ± 0.9 | 24.6 ± 1.1** | 24.6 ± 1.4* | 24.1 ± 1.0* |
| 8 | 56 | 23.3 ± 1.3 | 24.3 ± 1.2 | 24.5 ± 1.5 | 23.8 ± 1.1 |
| 9 | 63 | 22.6 ± 1.0 | 24.2 ± 1.0** | 23.8 ± 1.4 | 23.6 ± 0.9* |
| 10 | 70 | 23.2 ± 1.0 | 24.1 ± 0.7 | 24.6 ± 1.5* | 24.2 ± 0.9 |
| 11 | 76 | 23.1 ± 0.8 | 24.4 ± 1.0* | 24.9 ± 1.7* | 24.5 ± 1.1* |
| 12 | 84 | 23.3 ± 1.3 | 24.3 ± 1.0 | 24.9 ± 1.9 | 24.4 ± 1.1 |
| 13 | 91 | 23.2 ± 1.3 | 24.8 ± 0.9 | 25.4 ± 1.8 | 24.7 ± 1.1 |
| 14 | 98 | 23.7 ± 1.4 | 25.1 ± 1.0* | 25.5 ± 2.0 | 24.8 ± 1.2 |
| 15 | 105 | 23.5 ± 1.4 | 25.4 ± 0.8** | 25.9 ± 2.3* | 25.2 ± 1.1* |
| 17 | 120 | 24.2 ± 1.6 | 26.4 ± 1.2** | 26.9 ± 2.8* | 25.5 ± 1.1 |

*$0.01 < P \leq 0.05$
**$0.001 < P \leq 0.01$
***$P \leq 0.001$

TABLE 11

| | | BODY WEIGHT (g) | | | |
|---|---|---|---|---|---|
| WEEK | DAY | N-6 5 mg/kg | N-9 5 mg/kg | N-12 5 mg/kg | N-30 5 mg/kg |
| 0 | 0 | 20.3 ± 1.1 | 20.3 ± 0.7 | 20.5 ± 0.9 | 20.5 ± 0.7 |
| 0 | 1 | 21.2 ± 1.1 | 21.0 ± 1.1 | 21.3 ± 1.0 | 21.1 ± 0.9 |
| 0 | 3 | 20.8 ± 1.1 | 20.9 ± 1.0 | 21.0 ± 0.6 | 20.8 ± 0.7 |
| 0 | 5 | 20.5 ± 1.3 | 20.5 ± 1.1 | 20.5 ± 0.6 | 20.5 ± 0.9 |
| 1 | 8 | 20.3 ± 1.4 | 20.4 ± 0.8 | 20.1 ± 0.7 | 20.4 ± 0.8 |
| 1 | 11 | 21.3 ± 1.6 | 21.3 ± 1.1 | 21.3 ± 0.8 | 21.6 ± 1.0 |
| 2 | 14 | 22.0 ± 1.3 | 22.0 ± 1.1 | 22.0 ± 1.0 | 22.4 ± 1.0 |
| 3 | 21 | 22.4 ± 1.5 | 22.2 ± 1.0 | 22.2 ± 0.9 | 22.6 ± 1.1 |
| 4 | 29 | 23.2 ± 1.7 | 23.1 ± 1.1 | 22.7 ± 1.4 | 22.7 ± 1.0 |
| 5 | 36 | 23.8 ± 2.0 | 22.9 ± 1.6 | 22.9 ± 1.5 | 23.5 ± 0.9* |
| 6 | 42 | 24.4 ± 2.0* | 23.3 ± 1.5 | 22.7 ± 1.6 | 23.8 ± 1.2* |
| 7 | 49 | 24.8 ± 2.3* | 23.9 ± 1.6 | 23.5 ± 1.7 | 24.3 ± 1.4* |
| 8 | 56 | 24.7 ± 2.9 | 23.6 ± 1.7 | 23.6 ± 1.3 | 24.1 ± 1.7 |
| 9 | 63 | 24.4 ± 2.8 | 23.3 ± 1.5 | 23.5 ± 1.4 | 23.8 ± 1.9 |
| 10 | 70 | 24.7 ± 2.8 | 23.7 ± 1.7 | 23.7 ± 1.2 | 24.2 ± 1.9 |
| 11 | 76 | 25.3 ± 2.6 | 24.3 ± 1.8 | 24.0 ± 1.2 | 24.9 ± 1.7* |
| 12 | 84 | 25.1 ± 2.7 | 24.4 ± 1.9 | 24.0 ± 1.3 | 24.7 ± 1.9 |
| 13 | 91 | 25.8 ± 3.0 | 24.5 ± 1.5 | 24.3 ± 1.4 | 25.0 ± 1.9 |
| 14 | 98 | 25.9 ± 3.2 | 24.3 ± 1.5 | 24.4 ± 1.5 | 25.5 ± 2.1 |
| 15 | 105 | 26.0 ± 3.2 | 24.3 ± 1.5 | 24.4 ± 1.5 | 25.4 ± 2.3 |
| 17 | 120 | 26.8 ± 3.4 | 24.9 ± 1.4 | 24.9 ± 1.9 | 25.9 ± 2.4 |

*$0.01 < P \leq 0.05$
**$0.001 < P \leq 0.01$
***$P \leq 0.001$

Example 7

(1) Collection of polymorphonuclear leukocyte 120 ml/kg of 1% casein solution was administered intraperitoneally to Wister male rats (the body weight: 250–300 g), and the rats were bleeded to the death. The casein solution was recovered from the abdomin of the rats and the abdomin was washed with a phosphate buffer solution several times whereby the cell suspensions containing $2 \times 10^{-7}$ cells/ml of cells were prepared.

(2) Experimental materials

The partial hydrolysis products of colominic acid were prepared by hydrolysis of colominic acid with an acid and purification.

(3) Measurement of chemotactic activity of neutrophil

The chemotactic activity of neutrophil was measured by the Boyden's method (Boyden, S., Journal of Experimental Mediciene, Vol. 115, (1962) pages 453–466). That is, about 400 μl of the chemotactic factor (FMLP: Formyl-Met-Leu-Phe or a serum activated with zymosan) was introduced into a lower chamber, and a polycarbonate filter with 2 μm of pore size was placed on the lower chamber so as to prevent bubbles from invading. Then the lower chamber was fixed on an upper chamber. The cell suspension which 695 prepared in advance was mixed homogeneously with the tested drug (N-6), and 300 μl of the mixed solution was added to the upper chamber followed by culturing at 37° C. in an atmosphere containing 5% $CO_2$ for 90 minutes. After the culture, the solution in the upper chamber was removed and washed with a phosphate-buffered solution several times. Then the solution in the lower chamber together with the filter were obtained. After suspension of the cells in the solution, the number of the cells was counted by a hemocytometer and the suppression rate of chemotaxis was calculated.

(4) Experimental Result

As seen from Table 12, the chemotaxis of neutrophil was suppressed by N-6 in a dose-dependent manner.

TABLE 12

| | Chemotactic Factor | |
|---|---|---|
| TESTED DRUGS | FMLP | zymosan-activated serum |
| N-6 | | |
| $5.0 \times 10^{18}$ M | 47 ± 3.6% | 47 ± 3.6% |
| $5.0 \times 10^{16}$ M | 66 ± 7.2% | 66 ± 7.2% |
| $5.0 \times 10^{14}$ M | 67 ± 2.4% | 26 ± 12.7% |
| $5.0 \times 10^{12}$ M | 64 ± 1.8% | 44 ± 9.2% |
| $5.0 \times 10^{10}$ M | 64 ± 1.8% | 50 ± 8.0% |
| $5.0 \times 10^{8}$ M | 82 ± 2.0% | 47 ± 8.3% |
| $5.0 \times 10^{7}$ M | 85 ± 1.5% | 61 ± 3.3% |
| Methylprednisolone | | |
| $5.0 \times 10^{7}$ M | 47 ± 3.6% | 26 ± 6.0% |

Example 8

In accordance with the same procedures of Example 7 except that N-4, N-5, N-6, N-7, N-8 and N-9 were used as the tested drug and the concentrations of the tested drugs were $5 \times 10^{-7}$ M, the suppression rates of chemotaxis of neutrophil by the serum activated with zymosan were measured. The results are shown in Table 13.

TABLE 13

| TESTED DRUGS | SUPPRESSION RATE AT $5 \times 10^{-10}$ M C % |
|---|---|
| N-4 | 45.1 ± 0.4 |
| N-5 | 51.1 ± 9.2 |
| N-6 | 64.2 ± 1.7 |
| N-7 | 56.8 ± 5.3 |
| N-8 | 46.8 ± 9.6 |
| N-9 | 44.4 ± 5.4 |

What we claim is:

1. A method for the treatment of a renal disease, said method comprising administering an effective amount to treat netphritis of a colominic acid or a compound represented by formula

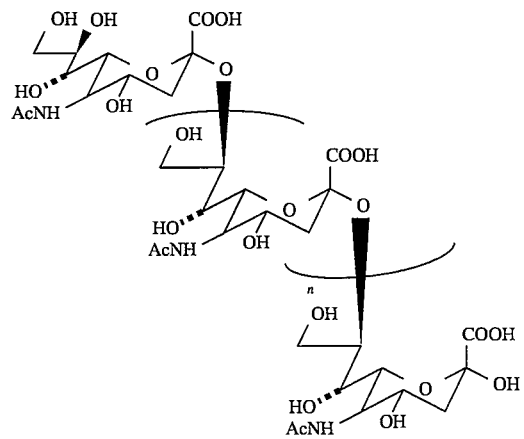

wherein n is an integer from 0 to 10 or a pharmaceutically acceptable salt thereof to a patient in need of such treatment.

2. The method as claimed in claim 1 wherein n is an integer of from 1 to 7.

3. A method for the treatment of hepatitis, said method comprising administering an effective amount to treat hepatitis of colominic acid or a compound represented by the formula

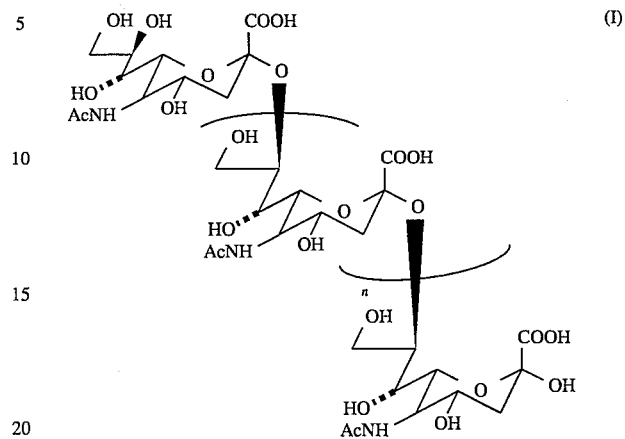

wherein n is an integer of from 0 to 10 or a pharmaceutically acceptable salt thereof, to a patient in need of such treatment.

4. The method as claimed in claim 3 wherein n is an integer of from 1 to 7.

* * * * *